(12) United States Patent
Zhang et al.

(10) Patent No.: US 9,872,823 B2
(45) Date of Patent: *Jan. 23, 2018

(54) METHOD FOR IMPROVING FASTNESS PROPERTIES OF FLUORESCENT COMPOUNDS ON HAIR

(71) Applicant: Noxell Corporation, Hunt Valley, MD (US)

(72) Inventors: Guiru Zhang, Lebanon, OH (US); Bryan Patrick Murphy, Loveland, OH (US)

(73) Assignee: Noxell Corporation, Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/072,527

(22) Filed: Mar. 17, 2016

(65) Prior Publication Data

US 2016/0271037 A1 Sep. 22, 2016

Related U.S. Application Data

(60) Provisional application No. 62/135,532, filed on Mar. 19, 2015.

(51) Int. Cl.
| | |
|---|---|
| *A61K 8/49* | (2006.01) |
| *A61Q 5/08* | (2006.01) |
| *A61Q 5/10* | (2006.01) |
| *A61C 5/10* | (2006.01) |
| *A61Q 5/06* | (2006.01) |

(52) U.S. Cl.
CPC ............... *A61K 8/492* (2013.01); *A61C 5/10* (2013.01); *A61K 8/49* (2013.01); *A61Q 5/065* (2013.01); *A61Q 5/08* (2013.01); *A61K 2800/434* (2013.01)

(58) Field of Classification Search
CPC ...... A61K 8/49; A61K 8/4926; A61K 8/4946; A61K 8/44; A61K 8/41; A61K 8/411; A61K 8/494; A61K 8/4953; A61K 2800/434; A61K 8/496; A61K 8/894; A61K 2800/43; A61K 8/361; A61K 8/416; A61K 8/418

See application file for complete search history.

(56) References Cited

U.S. PATENT DOCUMENTS

| | | |
|---|---|---|
| 5,708,151 A | 1/1998 | Mockli |
| 5,733,343 A | 3/1998 | Mockli |
| 5,919,273 A | 7/1999 | Rondeau et al. |
| 6,001,135 A | 12/1999 | Rondeau |
| 6,368,360 B2 | 4/2002 | Samain |
| 6,997,963 B2 | 2/2006 | Guerin |
| 7,172,633 B2 | 2/2007 | Samain et al. |
| 7,198,650 B2 * | 4/2007 | Pourille-Grethen ..... A61K 8/44 132/202 |
| 7,300,471 B2 | 11/2007 | Greaves et al. |
| 7,507,260 B2 | 3/2009 | Rondeau |
| 7,513,917 B2 | 4/2009 | Pasquier |
| 7,794,509 B2 | 9/2010 | Cremer |
| 8,444,715 B2 | 5/2013 | Lewis |
| 8,562,693 B2 | 10/2013 | Daubresse et al. |
| 8,685,114 B2 | 4/2014 | Daubresse et al. |
| 8,758,451 B2 | 6/2014 | Lewis et al. |
| 8,932,370 B2 | 1/2015 | Lewis et al. |
| 9,248,086 B2 | 2/2016 | Lewis et al. |
| 2003/0177591 A1 | 9/2003 | Mockli |
| 2004/0049020 A1 | 3/2004 | Mockli |
| 2004/0168265 A1 | 9/2004 | Eliu et al. |
| 2004/0187225 A1 | 9/2004 | Vidal et al. |
| 2004/0244125 A1 | 12/2004 | Mockli |
| 2005/0154195 A1 | 7/2005 | Eliu |
| 2005/0191253 A1 | 9/2005 | Gourlaouen et al. |
| 2006/0010617 A1 | 1/2006 | Gourlaouen et al. |
| 2006/0016025 A1 | 1/2006 | Greaves et al. |
| 2006/0026776 A1 | 2/2006 | Mockli |
| 2006/0174423 A1 | 8/2006 | Rothe et al. |
| 2007/0125261 A1 | 6/2007 | Daubresse et al. |

(Continued)

FOREIGN PATENT DOCUMENTS

| | | |
|---|---|---|
| EP | 0850636 A1 | 7/1998 |
| EP | 1464322 A1 | 10/2004 |

(Continued)

OTHER PUBLICATIONS

"International Application Serial No. PCT/US2016/022866, International Search Report dated Oct. 31, 2016", 5 pgs.
"International Application Serial No. PCT/US2016/022866, Written Opinion dated Oct. 31, 2016", 7 pgs.
"U.S. Appl. No. 15/072,512, Final Office Action dated Jul. 26, 2017", 5 pgs.
"U.S. Appl. No. 15/072,512, Non Final Office Action dated Jan. 9, 2017", 8 pgs.
"U.S. Appl. No. 15/072,512, Response filed Jul. 10, 2017 to Non Final Office Action dated Jan. 9, 2017", 5 pgs.
"U.S. Appl. No. 15/072,518, Non Final Office Action dated Nov. 21, 2016", 11 pgs.
"U.S. Appl. No. 15/072,518, Notice of Allowance dated Aug. 1, 2017", 10 pgs.
"U.S. Appl. No. 15/072,518, Response filed Apr. 17, 2017 to Non Final Office Action dated Nov. 21, 2016", 10 pgs.

(Continued)

*Primary Examiner* — Audrea Buckley
(74) *Attorney, Agent, or Firm* — Schwegman Lundberg & Woessner, P.A.

(57) ABSTRACT

Described herein is a method of treating the hair. The method includes applying to the hair a hair treatment composition including one or more fluorescent compounds and rinsing the hair with water. The one or more fluorescent compounds each include a fluorophore, one or two permanent cations, and one to four incipient cations. The incipient cations are pendant to the core structure and are neutral. The one or more fluorescent compounds enter the hair shaft after the hair treatment composition is applied to the hair. The hair treatment composition has a pH of from about 7 to about 11. The pH of the hair after rinsing is from about 3.5 to about 6. The rinsing of the hair causes one or more of the one to four incipient cations to change from neutral to positively charged inside of the hair shaft.

10 Claims, No Drawings

(56) References Cited

U.S. PATENT DOCUMENTS

| | | |
|---|---|---|
| 2007/0214580 A1 | 9/2007 | Eliu et al. |
| 2009/0089939 A1 | 4/2009 | Greaves et al. |
| 2009/0293208 A1 | 12/2009 | Eliu et al. |
| 2011/0011417 A1 | 1/2011 | Greaves et al. |
| 2011/0136134 A1 | 6/2011 | Kudo |
| 2011/0142892 A1 | 6/2011 | Daly |
| 2012/0210520 A1 | 8/2012 | Lim et al. |
| 2015/0101132 A1 | 4/2015 | David |
| 2015/0113742 A1 | 4/2015 | David |
| 2016/0106648 A1 | 4/2016 | Lewis et al. |
| 2016/0271036 A1 | 9/2016 | Zhang et al. |
| 2016/0271038 A1 | 9/2016 | Zhang et al. |
| 2016/0271039 A1 | 9/2016 | Zhang et al. |

FOREIGN PATENT DOCUMENTS

| | | |
|---|---|---|
| EP | 2039724 A1 | 3/2009 |
| FR | 2857258 A1 | 1/2005 |
| FR | 2898903 A1 | 9/2007 |
| WO | WO9720545 A1 | 6/1997 |
| WO | WO-2004000257 A2 | 12/2003 |
| WO | WO-2013174987 A2 | 11/2013 |
| WO | WO-2016/149493 A2 | 9/2016 |
| WO | WO-2016149490 A1 | 9/2016 |
| WO | WO-2016149491 A1 | 9/2016 |
| WO | WO-2016149495 A1 | 9/2016 |

OTHER PUBLICATIONS

"U.S. Appl. No. 15/072,542, Non Final Office Action dated Nov. 22, 2016", 13 pgs.

"U.S. Appl. No. 15/072,542, Notice of Allowance dated Aug. 2, 2017", 10 pgs.

"U.S. Appl. No. 15/072,542, Response filed Mar. 27, 2017 to Non Final Office Action dated Nov. 22, 2016", 11 pgs.

"International Application Serial No. PCT/US2016/022862, International Search Report dated Aug. 9, 2016", 6 pgs.

"International Application Serial No. PCT/U52016/022862, Written Opinion dated Aug. 9, 2016", 12 pgs.

"International Application Serial No. PCT/US2016/022864, International Search Report dated Jun. 16, 2016", 6 pgs.

"International Application Serial No. PCT/U52016/022864, Written Opinion dated Jun. 16, 16", 11 pgs.

"International Application Serial No. PCT/US2016/022869, International Search Report dated Jun. 16, 2016", 6 pgs.

"International Application Serial No. PCT/US2016/022869, Written Opinion dated Jun. 16, 2016", 8 pgs.

Greaves, Andrew, et al., "EP 2039724, published Mar. 25, 2009, English machine translation obtained on Nov. 15, 2016", (Mar. 25, 2009), 28 pgs.

Pourille-Grethen, Chrystel, et al., "EP1464322, published Oct. 6, 2004, English machine translation obtained on Nov. 15, 2016", (Oct. 6, 2004), 55 pgs.

"U.S. Appl. No. 15/072,512, Response filed Sep. 26, 2017 to Final Office Action dated Jul. 26, 2017", 5 pgs.

"U.S. Appl. No. 15/072,518, Examiner Interview Summary dated Aug. 24, 2017", 3 pgs.

"U.S. Appl. No. 15/072,518, PTO Response to Rule 312 Communication dated Aug. 31, 2017", 2 pgs.

"U.S. Appl. No. 15/072,518, Response filed Aug. 21, 2017 to Notice of Allowance dated Aug. 1, 2017", 8 pgs.

"U.S. Appl. No. 15/072,542, Examiner Interview Summary dated Aug. 22, 2017", 3 pgs.

"U.S. Appl. No. 15/072,542, PTO Response to Rule 312 Communication dated Aug. 30, 2017", 2 pgs.

U.S. Appl. No. 15/072,512, filed Mar. 17, 2016, Method for Improving Acid Perspiration Resistance of Fluorescent Compounds on Hair.

U.S. Appl. No. 15/072,518m filed Mar. 17, 2016, Fluorescent Compounds for Treating Hair.

U.S. Appl. No. 15/072,542, filed Mar. 17, 2016, Acid Perspiration Resistant Fluorescent Compounds for Treating Hair.

\* cited by examiner

METHOD FOR IMPROVING FASTNESS PROPERTIES OF FLUORESCENT COMPOUNDS ON HAIR

FIELD OF THE INVENTION

Provided is a method of treating hair with one or more washfast fluorescent compounds. The fluorescent compounds each have one to two permanent positive charges and one to four incipient cations. A decrease in pH when rinsing the hair causes one or more of the incipient cations to change from neutral to positively charged inside of the hair shaft, making them more resistant to water and shampoo.

BACKGROUND OF THE INVENTION

The unique physical properties of fluorophores allow them to provide optical effects on hair that cannot be matched by typical dyes. For example, the appearance of lightening for dark hair can be offered by optical brighteners. Brassiness in bleached hair can be minimized by fluorescent materials that emit green light which cancels the red components in brassy hair. Fashion shades that are only visible under black light can be achieved with fluorophores that absorb UV but emit visible light. Fluorophores provide many desirable effects on hair that cannot be provided by direct dyes and oxidative dyes alike. Understanding the factors contributing to washfastness would allow us to find ways to enhance the washfastness properties of fluorescent materials.

The alteration of the appearance of keratinous fibers, in particular human hair, by the application of fluorophores has not yet become a common practice in the salon or consumer's homes. However, the number of patent applications and granted patents in this particular field is abundant. According to these publications, applying fluorophores been done mostly with anionic, cationic or zwitterionic fluorescent materials. In some cases, a mercapto group is attached to the fluorophore via a pendant group to allow the fluorescent material to be covalently bonded to keratin proteins to enhance the washfastness of the fluorophore. In some other cases, two fluorophores, typically identical, are linked together by a tethering group to produce a polycationic dimer. The challenge is to still meet all of the other requirements for materials that improve the appearance of hair (e.g., little or no bleeding from the hair when it is wet, evenness, etc.)

We have learned that there are drawbacks in each one of the above approaches to provide consumers an easy and pleasant experience. Anionic and zwitterionic fluorophores are not washfast as they constantly bleed out of hair fibers. Cationic fluorophores are better than anionic and zwitterionic counterparts in bleeding and washfastness, but they would still fade with repetitive use of shampoo for hair cleansing. The approach through covalent bonding via disulfide bonds (reactive fluorophores) does not differentiate proteins in hair from skin. Dimerization of the fluorophores would increase the number of binding sites that minimizes bleeding and loss caused by rinsing by providing stronger hair-fluorophore interactions. However, the same strong binding force to the cuticle also prevents the fluorophores from penetrating deep into the cortex of hair, because it is difficult for fluorophores with multiple positive charges to diffuse through negatively charged networks of keratin proteins. Additionally, since polycationic fluorophores remain bound to the hair surface rather than penetrating into the fiber, it is difficult to produce intense effects due to limited binding sites on the surface of hair. The fluorophores would also be at least twice as big as the monomer, which can become another obstacle for penetration.

SUMMARY OF THE INVENTION

Described herein is a method of imparting improved washfastness when treating the hair with fluorescent compounds, the method comprising (a) applying to the hair a hair treatment composition comprising one or more fluorescent compounds, the one or more fluorescent compounds each comprising (i) a fluorophore; (ii) one or two permanent cations, wherein the permanent cations are pendant to the fluorophore or part of the fluorophore, and wherein the fluorophore and the permanent cations form a core structure; (iii) one to four incipient cations, wherein the incipient cations are pendant to the core structure, and wherein the incipient cations are neutral; wherein the one or more fluorescent compounds enter the hair shaft after the composition is applied to the hair; and wherein the hair treatment composition has a pH of from about 7 to about 11; (b) rinsing the hair with water; wherein the pH of the hair after rinsing is from about 3.5 to about 6; and wherein the rinsing of the hair causes one or more of the one to four incipient cations to change from neutral to positively charged inside of the hair shaft.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. When more than one composition is used during a treatment, as in mixing of the components of a typical oxidative dye product, the total weight to be considered is the total weight of all the compositions applied on the hair simultaneously (i.e. the weight found "on head") unless otherwise specified. The term "weight percent" may be denoted as "wt. %" herein.

As used herein, the term "hair" to be treated may be "living" i.e. on a living body or may be "non-living" i.e. in a wig, hairpiece or other aggregation of non-living keratinous fibers. Mammalian, particularly human, hair is preferred. However, wool, fur, and other keratin containing fibers are suitable substrates for the compositions according to the present invention.

As used herein, the term "pendant group" means a group of atoms attached to the core structure or fluorophore. As described herein, the pendant group itself is not a fluorophore, although it may influence the emission spectrum of the fluorophore. The pendant group may be further classified as an anchoring group or a hydrophobic group. A hydrophobic group (hydrophobe) is typically a carbon chain. An anchoring group is a group attached to either a permanent cation or incipient cation, occasionally it is attached to both a permanent cation and one or more incipient cations.

As used herein, the term "fluorophore" means the part of the fluorescent compound responsible for providing the optical effect.

As used herein, the term "fluorescent compound" means a fluorescent material used in a process in which fluorescent molecules are attracted by physical forces at the molecular level to a textile or substrate such as the hair. As opposed to reactive fluorescent materials, there is no covalent bond formation between the fluorescent compound and the substrate. The fluorescent compound does not undergo a chemical transformation before and after the treatment process.

As used herein, the term "core structure" means the fluorophore including one or two permanent cations that are pendant to the fluorophore or part of the fluorophore. In an embodiment, the fluorophore is charged. In an embodiment, the fluorophore is not charged as the permanent cation is pendant to the fluorophore.

As used herein, the term "pendant" means when a functional group is linked to a core structure via covalent bond.

As used herein, the term "incipient cation" means a functional group that goes from neutral to positively charged due to protonation during a change in pH.

As used herein, the term "non-anionic foaming agent" is a material that facilitates formation of foam. The term typically refers to a surfactant which, when present in small amounts, reduces the surface tension of a liquid or increases its colloidal stability by inhibiting coalescence of bubbles.

As used herein, the term "hydrophobic moieties" means either hydrophobic molecules or hydrophobic functional groups.

The hair brightening compositions of the present invention comprise one or more washfast fluorescent compounds, optionally, direct dyes and oxidative dyes as well.

With regards to the fluorescent compounds described herein, numerous tautomeric compounds may be involved. Thus, for example, 2-mercaptopyridine (I) may exist under known conditions in the pyridine-2-thione tautomer form (II).

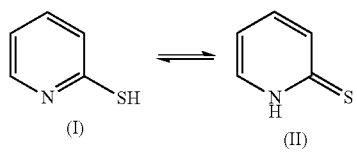

It is to be understood that when this development refers to a particular structure, all of the reasonable additional tautomeric structures are included. In the art, tautomeric structures are frequently represented by one single structure and the method described herein follows this general practice.

It is also understood that within the scope of this invention, E, Z isomers may be involved. Thus, for example, (E)-diphenyldiazene (III) converts under known conditions to (Z)-diphenyldiazene (IV), which is also reversible.

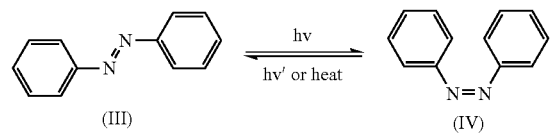

It is to be understood that when this development refers to a particular structure, all of the reasonable additional E, Z isomers are included.

I. Washfast Fluorescent Compounds

This invention relates to a novel approach where an incipient cation, typically an amino group or groups, is attached to the fluorophore in addition to the existing permanent cation(s) to overcome the problems encountered in previous attempts to make fluorescent materials more washfast. The fluorophore would typically carry only one or two permanent positive charges such as quaternary ammonium salts, pyridinium, imidazolium, thiazolium, oxazolium, triazolium, pyrimidinium, triazinium, tetrazolium phenoxazinium, phenazinium or an analogous cation under basic conditions for typical hair treatment applications. The amino group(s) would remain mostly neutral under the application conditions (pH 10~11) because the typical $pK_a$ of aliphatic amines falls between 9~10.5. The fluorophore would carry only one or two cationic charges under such conditions, which provides the needed affinity (Coulombic attraction) for optimized uptake without preventing penetration due to relatively low charge density and smaller size compared to polycationic fluorophores. However, once the application is done and hair is rinsed, pH inside hair drops back to its natural pH, which is weakly acidic, the amino group(s) attached to the fluorophore would be protonated to become an ammonium cation, which adds one or more binding sites to the fluorophore. The pH change functions as a convenient switch to turn on additional binding group(s) to make the fluorophores more washfast. Primary amines work the best when compared to secondary and tertiary amines for the following two reasons: 1. primary amines resist oxidation by hydrogen peroxide, while secondary and tertiary amines can be oxidized and lose their anchoring capability when used together with a bleaching agent; 2. the protonated primary ammonium cation is the smallest in size, which allows stronger interaction with anions in hair compared to secondary and tertiary amines with more steric hindrance. However, in applications without any oxidant, using secondary and tertiary amines as anchoring group would not be a problem.

In short, the said inventive technology minimizes the number of positive charges carried by the fluorophores under application conditions at high pH to facilitate penetration and deposition. After rinsing, however, the inventive technology maximizes the number of positive charges carried by the fluorophores at hair's natural pH to provide the desirable washfastness.

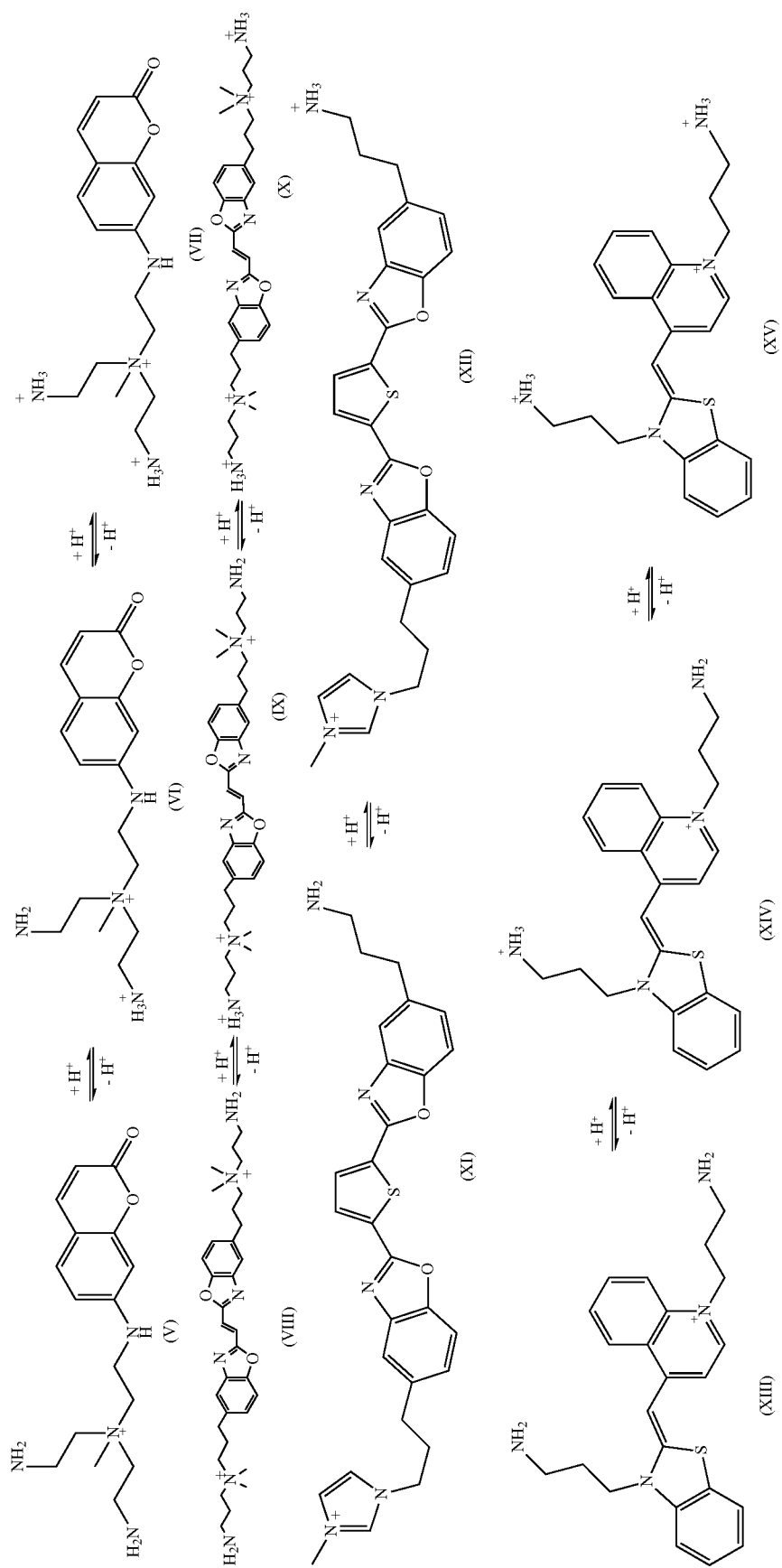

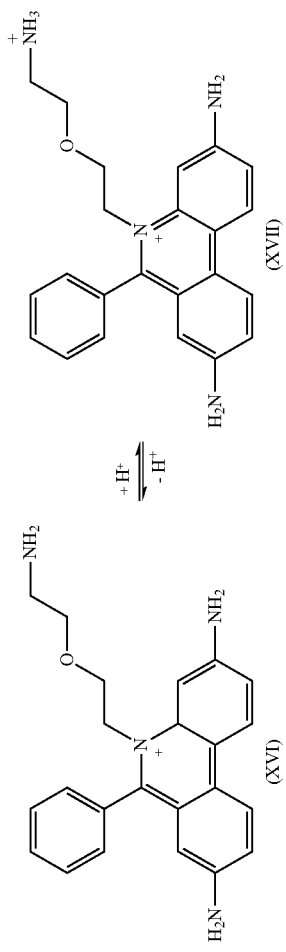
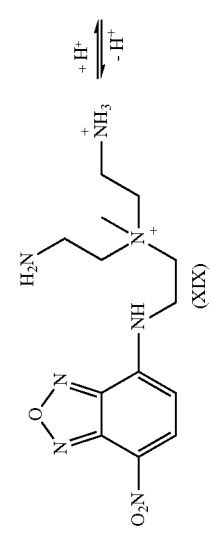
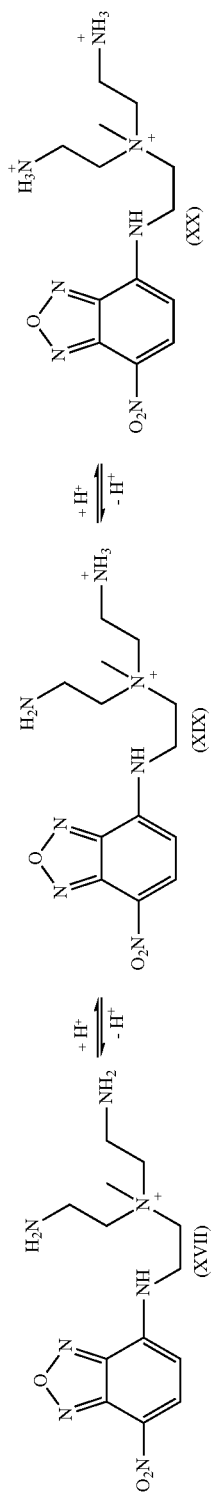

The linker groups, typically linear alkyl groups, would also function as modulators for the overall hydrophobicity of the fluorophore. One of the common drawbacks of using combinations of cationic fluorophores is fading shift in the emission spectrum as different fluorophores would be washed off hair at different rates, causing undesirable gradual shift in fluorescence over time.

Our technical approach minimizes this undesirable effect by incorporating identical charge patterns with similar overall hydrophobicity into different fluorophores to impart similar and enhanced washfastness profiles, so these inventive fluorophores are far more washfast than typical cationic fluorophores. The inventive fluorophores exhibit minimal loss of the effect, while maintaining the originally imparted emission spectrum and optical effects. The inventive compounds are substituted with one to two permanent cationic charges, preferably one, and one to four, preferably one or two, terminal amino groups and derivatives thereof, according to the following formula:
i. a fluorophore;
ii. one or two permanent cations, wherein the permanent cations are pendant to the fluorophore or part of the fluorophore, and wherein the fluorophore and the permanent cations form a core structure; and
iii. one to four incipient cations, wherein the one to four incipient cations are pendant to the core structure, and wherein the incipient cations are neutral at high pH.

The Markush structures of the inventive fluorescent materials can be represented in the following ways, but not limited to what is shown below:

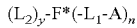  (XXI)

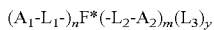  (XXII)

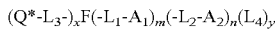  (XXIII)

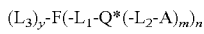  (XXIV)

  (XXV)

wherein
F is a fluorophore;
Q* is an organic cation;
* stands for a permanent cationic charge, it can also be part of a fluorophore bearing a cationic charge;
L is a linker or hydrophobic chain and;
A is the anchoring group, the fastness enhancer. It is typically a primary, secondary or tertiary amino group, preferably a primary amine. It is also a switch to allow the anchor to go between neutral and charged states when the pH in the surrounding environment changes.
n=1~4; m=1~4; n+m≤4; x=1~2; y=0~2.
In some embodiments, F is of formula XXVIa

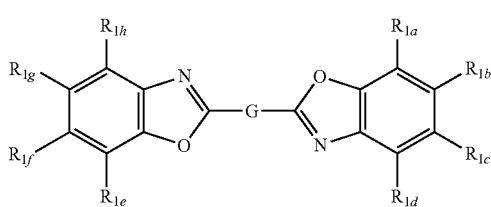

(XXVIa)

wherein
G is an alkenyl, polyalkenyl chain or aromatic ring system that conjugates the two benzoxazole moieties. G can be —(CH=CH)$_n$— with n=1~5, p-phenylene or 1,1'-biphenyl; and $R_{1a}$, $R_{1b}$, $R_{1c}$, $R_{1d}$, $R_{1e}$, $R_{1f}$, $R_{1g}$ and $R_{1h}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether; linker group L or linker group L with a primary, secondary or tertiary amino group attached; and At least one of $R_{1a}$, $R_{1b}$, $R_{1c}$, $R_{1d}$, $R_{1e}$, $R_{1f}$, $R_{1g}$ and $R_{1h}$ must be linker group L with a cationic moiety attached to it. The cationic group is a quaternary ammonium, imidazolium, pyridinium, oxazolium or thiazolium. It can also take on the following form as $L_1$-Q*(-$L_2$A)$_n$, where $L_1$ and $L_2$ can be the same or different, Q* is the cationic moiety, A is an amino group; and n is either 1 or 2; and The total number of permanent cationic charge among $R_{1a}$, $R_{1b}$, $R_{1c}$, $R_{1d}$, $R_{1e}$, $R_{1f}$, $R_{1g}$ and $R_{1h}$ is 1 or 2; the total number of amino groups among $R_{1a}$, $R_{1b}$, $R_{1c}$, $R_{1d}$, $R_{1e}$, $R_{1f}$, $R_{1g}$ and $R_{1h}$ is 1-4; the amino group can be primary, secondary or tertiary; and cosmetically acceptable salt thereof.

In some embodiments, L is of formula (XXVII)

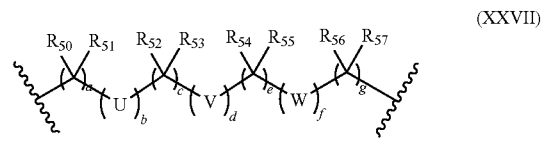

(XXVII)

wherein
L is covalently linked to the fluorophore F of formula (XXVIa); L can be linked to F either by its left-hand or right-hand side.

a, c, e and g are each independently an integer from 0-3, provided that the sum of a, c, e and g is greater than or equal to 2; b, d and f are each independently either 0 or 1; $R_{50}$, $R_{51}$, $R_{52}$, $R_{53}$, $R_{54}$, $R_{55}$, $R_{56}$ and $R_{57}$ are each independently hydrogen or $C_1$-$C_2$ alkyl group;
U is an aromatic ring, alkenyl or alkynyl moiety;
V is a hetero atom O, N or S;
W is a cyclic aliphatic ring.
In other embodiments, the fluorophore F is of formula (XXVIb);

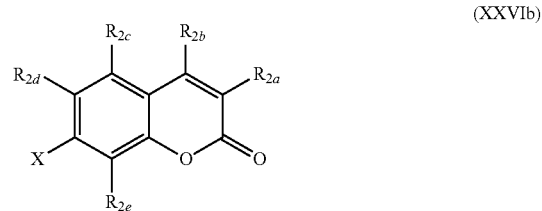

(XXVIb)

wherein
X can be $NR_{2f}R_{2g}$, $OR_{2h}$ or $SR_{2i}$.
$R_{2a}$, $R_{2b}$, $R_{2c}$, $R_{2d}$ and $R_{2e}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether; linker group L or linker group L with a primary, secondary or tertiary amino group attached; and $R_{2f}$, $R_{2g}$, $R_{2h}$ and $R_{2i}$ are each independently hydrogen, alkyl, substituted alkyl, aryl, a heterocyclic moiety, linker group L or linker group L with a primary, secondary or tertiary amino group attached; and One of $R_{2a}$, $R_{2b}$, $R_{2c}$, $R_{2d}$, $R_{2e}$, $R_{2f}$, $R_{2g}$, $R_{2h}$ and $R_{2i}$ must be linker group L with a cationic moiety attached to it. The cationic group is a quaternary ammonium, imidazolium, pyridinium, oxazolium or thiazolium. It can also take on the following form as $L_1$-$Q^*$(-$L_2$A)$_n$, where $L_1$ and $L_2$ can be the same or different, $Q^*$ is the cationic moiety, A is an amino group; and n is either 1 or 2; and The total number of permanent cationic charge among $R_{2a}$, $R_{2b}$, $R_{2c}$, $R_{2d}$, $R_{2e}$, $R_{2f}$, $R_{2g}$, $R_{2h}$ and $R_{2i}$ is 1 or 2; the total number of amino groups among $R_{2a}$, $R_{2b}$, $R_{2c}$, $R_{2d}$, $R_{2e}$, $R_{2f}$, $R_{2g}$, $R_{2h}$ and $R_{2i}$, is 1-4; the amino group can be primary, secondary or tertiary; and cosmetically acceptable salt thereof.

In other embodiments, the fluorophore F is of formula (XXVIc);

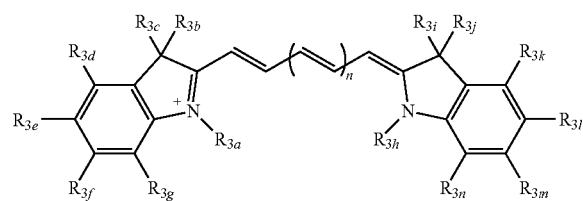

(XXVIc)

wherein $R_{3b}$, $R_{3c}$, $R_{3d}$, $R_{3e}$, $R_{3f}$, $R_{3g}$, $R_{3i}$, $R_{3j}$, $R_{3k}$, $R_{3l}$, $R_{3m}$ and $R_{3n}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L with or without a terminal amino group; and $R_{3a}$ and $R_{3h}$ are linker group L with a primary, secondary or tertiary amino group attached;

The total number of amino groups attached to $R_{3a}$, $R_{3h}$ is 1 or 2; the amino group can be primary, secondary or tertiary; and cosmetically acceptable salt thereof.

In other embodiments, the fluorophore F is of formula (XXVId);

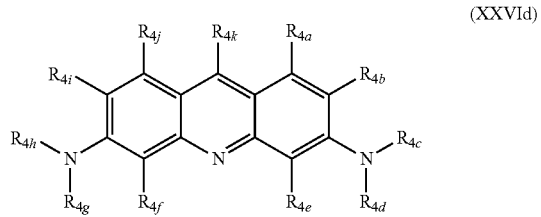

(XXVId)

wherein $R_{4a}$, $R_{4b}$, $R_{4e}$, $R_{4f}$, $R_{4i}$, $R_{4j}$, $R_{4k}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L with or without a terminal amino group; and $R_{4c}$, $R_{4d}$, $R_{4g}$ and $R_{4h}$ are each independently hydrogen, $C_1$-$C_8$ alkyl or linker group L with a primary, secondary or tertiary amino group attached. At least one of $R_{4c}$, $R_{4d}$, $R_{4g}$ and $R_{4h}$ must be linker group L with a cationic moiety attached to it. The cationic group is a quaternary ammonium, imidazolium, pyridinium, oxazolium or thiazolium. It can also take on the following form as $L_1$-$Q^*$(-$L_2$A)$_n$, where $L_1$ and $L_2$ can be the same or different, $Q^*$ is the cationic moiety, A is an amino group; and n is either 1 or 2; and The total number of permanent cationic charge among $R_{4c}$, $R_{4d}$, $R_{4g}$ and $R_{4h}$ is 1 or 2; the total number of amino groups among $R_{4c}$, $R_{4d}$, $R_{4g}$ and $R_{4h}$ is 1, 2, 3 or 4; the amino group can be primary, secondary or tertiary; and cosmetically acceptable salt thereof.

In other embodiments, the fluorophore F is of formula (XXVIe);

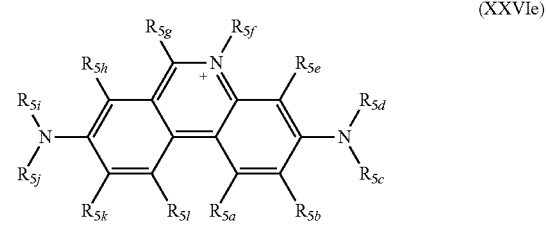

(XXVIe)

wherein $R_{5a}$, $R_{5b}$, $R_{5c}$, $R_{5h}$, $R_{5k}$ and $R_{5l}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{5g}$ is an aryl group which can be substituted or unsubstituted phenyl, naphthyl, pyridinyl, pyrimidinyl, triazinyl, thienyl, thiazolyl, imidazolyl, oxazolyl or indolyl; and $R_{5f}$ is linker group L with a primary, secondary or tertiary amino group attached; and $R_{5c}$, $R_{5d}$, $R_{5i}$ and $R_{5j}$ are each independently hydrogen, $C_1$-$C_8$ alkyl or linker group L with a primary, secondary or tertiary amino group attached; and The total number of amino groups among $R_{5c}$, $R_{5d}$, $R_{5f}$, $R_{5i}$ and $R_{5j}$ is 1, 2, 3, or 4; the amino group can be primary, secondary or tertiary; and cosmetically acceptable salt thereof.

In other embodiments, the fluorophore F is of formula (XXVIf);

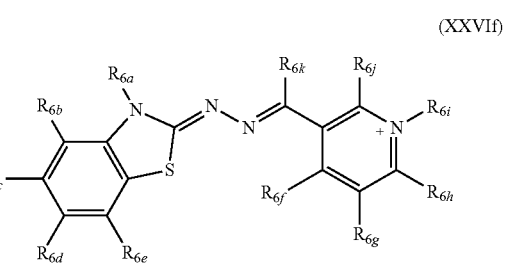

(XXVIf)

wherein $R_{6b}$, $R_{6c}$, $R_{6d}$, $R_{6e}$, $R_{6f}$, $R_{6g}$, $R_{6h}$, $R_{6j}$ and $R_{6k}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{6a}$ and $R_{6i}$ are each independently, $C_1$-$C_8$ alkyl or linker group L with a primary, secondary or tertiary amino group attached; and The total number of amino groups in $R_{6a}$ and $R_{6i}$ is 1 or 2; amino group can be primary, secondary or tertiary; and cosmetically acceptable salt thereof.

In other embodiments, the fluorophore F is of formula (XXVIg);

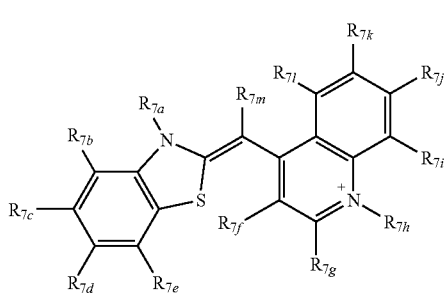
(XXVIg)

wherein $R_{7b}$, $R_{7c}$, $R_{7d}$, $R_{7e}$, $R_{7f}$, $R_{7g}$, $R_{7i}$, $R_{7j}$ $R_{7k}$, $R_{7l}$ and $R_{7m}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{7a}$ and $R_{7h}$ are each independently, $C_1$-$C_8$ alkyl or linker group L with a primary, secondary or tertiary amino group attached; and The total number of amino groups in $R_{7a}$ and $R_{7h}$ is 1 or 2; amino group can be primary, secondary or tertiary; and cosmetically acceptable salt thereof.

In other embodiments, the fluorophore F is of formula (XXVIh);

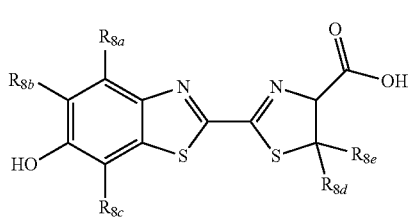
(XXVIh)

wherein $R_{8b}$ and $R_{8c}$ are halogen, hydrogen, alkyl, halogen substituted alkyl or cyano; and $R_{8a}$, $R_{8d}$ and $R_{8e}$ are each independently hydrogen, $C_1$-$C_8$ alkyl or linker group L with a primary, secondary or tertiary amino group attached. At least one of $R_{8a}$, $R_{8d}$ and $R_{8e}$ must be linker group L with a cationic moiety attached to it. The cationic group is a quaternary ammonium, imidazolium, pyridinium, oxazolium or thiazolium. It can also take on the following form as $L_1$-$Q^*$(-$L_2$A)$_n$, where $L_1$ and $L_2$ can be the same or different, $Q^*$ is the cationic moiety, A is an amino group; and n is either 1 or 2; and The total number of permanent cationic charge among $R_{8a}$, $R_{8d}$ and $R_{8e}$ is 1 or 2; the total number of amino groups among $R_{4c}$, $R_{4d}$, $R_{4g}$ and $R_{4h}$ is 1, 2, 3 or 4; the amino group can be primary, secondary or tertiary; and cosmetically acceptable salt thereof.

In other embodiments, the fluorophore F is of formula (XXVIi);

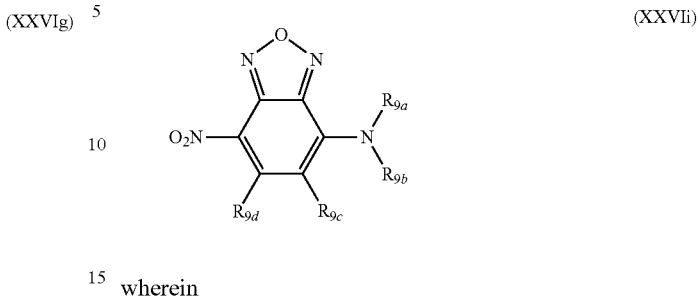
(XXVIi)

wherein $R_{9c}$ and $R_{9d}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{9a}$ and $R_{9b}$ are each independently hydrogen, $C_1$-$C_8$ alkyl or linker group L with a primary, secondary or tertiary amino group attached. At least one of $R_{9a}$ and $R_{9b}$ must be linker group L with a cationic moiety attached to it. The cationic group is a quaternary ammonium, imidazolium, pyridinium, oxazolium or thiazolium. It can also take on the following form as $L_1$-$Q^*$(-$L_2$A)$_n$, where $L_1$ and $L_2$ can be the same or different, $Q^*$ is the cationic moiety, A is an amino group; and n is either 1 or 2; and The total number of permanent cationic charge in $R_{9a}$ and $R_{9b}$ is 1 or 2; the total number of amino groups in $R_{9a}$ and $R_{9b}$ is 1, 2, 3 or 4; the amino group can be primary, secondary or tertiary; and cosmetically acceptable salt thereof.

In other embodiments, the fluorophore F is of formula (XXVIj);

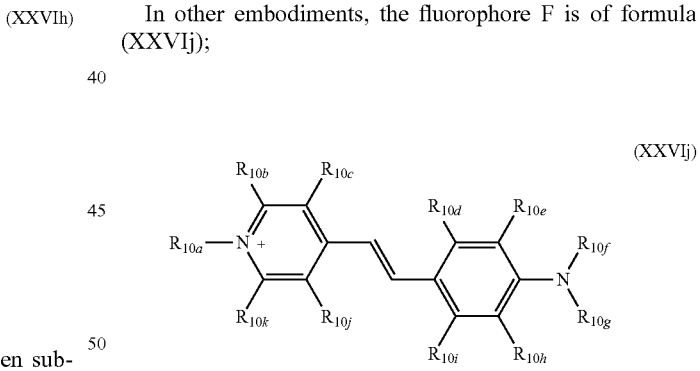
(XXVIj)

wherein $R_{10b}$, $R_{10c}$, $R_{10d}$, $R_{10e}$, $R_{10h}$, $R_{10i}$, $R_{10j}$ and $R_{10k}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{10a}$, $R_{10f}$ and $R_{10g}$ are each independently, $C_1$-$C_8$ alkyl or linker group L with a primary, secondary or tertiary amino group attached; and The total number of amino groups in $R_{10a}$, $R_{10f}$ and $R_{10g}$ is 1 to 3; amino group can be primary, secondary or tertiary; and cosmetically acceptable salt thereof.

In other embodiments, the fluorophore F is of formula (XXVIk);

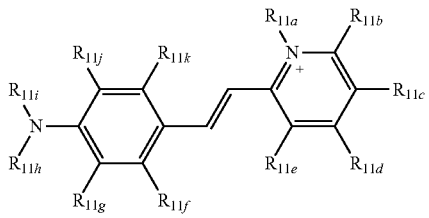

(XXVIk)

wherein $R_{11b}$, $R_{11c}$, $R_{11d}$, $R_{11e}$, $R_{11f}$, $R_{11g}$, $R_{11j}$ and $R_{11k}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{11a}$, $R_{11h}$ and $R_{11i}$ are each independently, $C_1$-$C_8$ alkyl or linker group L with a primary, secondary or tertiary amino group attached; and The total number of amino groups in $R_{11a}$, $R_{11h}$ and $R_{11i}$ is 1 to 3; amino group can be primary, secondary or tertiary; and cosmetically acceptable salt thereof.

In other embodiments, the fluorophore F is of formula (XXVII);

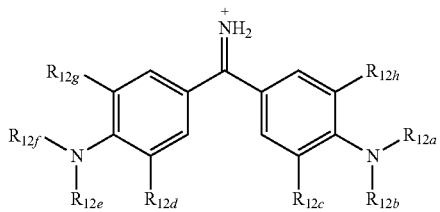

(XXVII)

wherein $R_{12c}$, $R_{12d}$, $R_{12g}$ and $R_{12h}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{12a}$, $R_{12b}$, $R_{12e}$ and $R_{12f}$ are each independently, $C_1$-$C_8$ alkyl or linker group L with a primary, secondary or tertiary amino group attached; and The total number of amino groups in $R_{12a}$, $R_{12b}$, $R_{12e}$ and $R_{12f}$ is 1 to 4; amino group can be primary, secondary or tertiary; and cosmetically acceptable salt thereof.

In other embodiments, the fluorophore F is of formula (XXVIm);

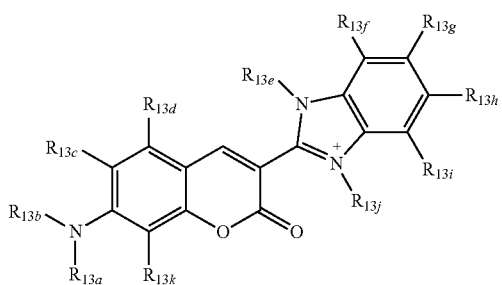

(XXVIm)

wherein $R_{13c}$, $R_{13d}$, $R_{13f}$, $R_{13g}$, $R_{13h}$, $R_{13i}$, and $R_{13k}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{13a}$, $R_{13b}$, $R_{13e}$ and $R_{13j}$ are each independently, $C_1$-$C_8$ alkyl or linker group L with a primary, secondary or tertiary amino group attached; and The total number of amino groups in $R_{13a}$, $R_{13b}$, $R_{13e}$ and $R_{13j}$ is 1 to 4; amino group can be primary, secondary or tertiary; and cosmetically acceptable salt thereof.

In other embodiments, the fluorophore F is of formula (XXVIn);

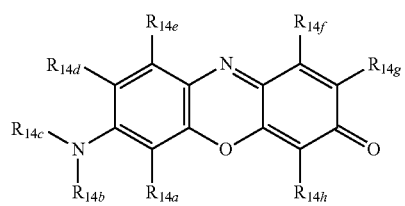

(XXVIn)

wherein $R_{14a}$, $R_{14d}$, $R_{14e}$, $R_{14f}$, $R_{14g}$ and $R_{13ih}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{14b}$ and $R_{14c}$ are each independently, hydrogen, $C_1$-$C_8$ alkyl or linker group L with a primary, secondary or tertiary amino group attached. At least one of $R_{14b}$ and $R_{14c}$ must be linker group L with a cationic moiety attached to it. The cationic group is a quaternary ammonium, imidazolium, pyridinium, oxazolium or thiazolium. It can also take on the following form as $L_1$-Q*(-L2A)$_n$, where $L_1$ and $L_2$ can be the same or different, Q* is the cationic moiety, A is an amino group; and n is either 1 or 2; and The total number of amino groups in $R_{14b}$ and $R_{14c}$ is 1 to 4; amino group can be primary, secondary or tertiary; and cosmetically acceptable salt thereof.

In other embodiments, the fluorophore F is of formula (XXVIo);

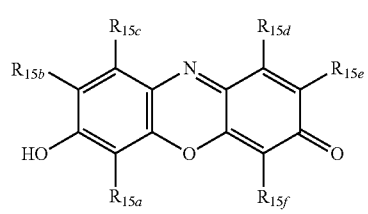

(XXVIo)

wherein $R_{15a}$, $R_{15b}$, $R_{15c}$, $R_{15d}$, $R_{15e}$ and $R_{15f}$ are each independently hydrogen, alkyl, halogen substituted alkyl, alkenyl, alkynyl, aryl, hydroxyl alkyl, alkoxy, aryloxy, acyl, halogen, nitro, nitroso, cyano, a heterocyclic moiety, thioether or are attached to linker L; and $R_{15a}$, $R_{15b}$, $R_{15c}$, $R_{15d}$, $R_{15e}$ and $R_{15f}$ can also be each independently, $C_1$-$C_8$ alkyl or linker group L with a primary, secondary or tertiary amino group attached; and At least one of $R_{15a}$, $R_{15b}$, $R_{15c}$, $R_{15d}$, $R_{15e}$ and $R_{15f}$ must be linker group L with a cationic moiety attached to it. The cationic group is a quaternary ammonium, imidazolium, pyridinium, oxazolium or thiazolium. It can also take on the following form as $L_1$-$Q^*$(-$L_2$A)$_n$, where $L_1$ and $L_2$ can be the same or different, $Q^*$ is the cationic moiety, A is an amino group; and n is either 1 or 2; and The total number of amino groups in $R_{15a}$, $R_{15b}$, $R_{15c}$, $R_{15d}$, $R_{15e}$ and $R_{15f}$ is 1 to 4; amino group can be primary, secondary or tertiary; and cosmetically acceptable salt thereof.

Example 1

In example 1, the permanent charge is part of the fluorophore and resides on the indolium moiety. The incipient cations are linked to the fluorophore via propylene groups.

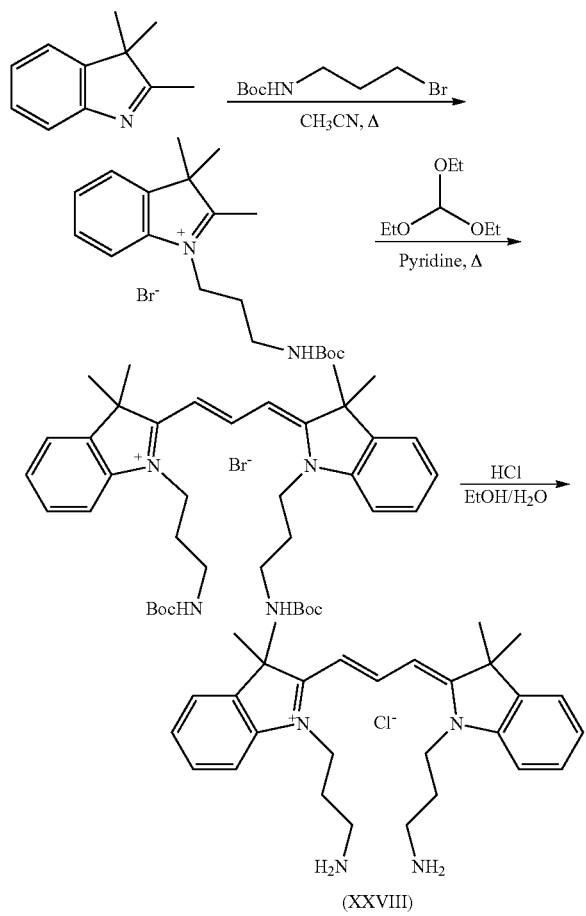

Neat 2,3,3-trimethylindolenine (1.6 g) and 3-(Boc-amino) propyl bromide (2.4 g, 1.0 eq.) were mixed, magnetically stirred and heated to 100° C. for 3 hours. After cooling, triethoxymethane (0.74 g, 0.5 eq.) and pyridine (50 ml) were added to the reaction flask. The reaction mixture was refluxed for 3 hours, after which pyridine was evaporated in vacuo. The desired violet fluorescent compound was purified on preparative HPLC with C18 reverse phase column and water/methanol (with 0.1% TFA) as mobile phase. The final product (XXVIII) was obtained after Boc group was removed by ethanolic HCl followed by evaporation. $^1$H NMR: (600.1 MHz, DMSO-$d_6$) δ=1.73 (12H, s), 2.02-2.07 (4H, m), 2.94-2.97 (4H, m), 4.21 (4H, br t), 6.50 (2H, d, J=13.6 Hz), 7.33-7.36 (2H, m), 7.47-7.50 (2H, m), 7.53 (2H, d, J=8.0 Hz), 7.67-7.72 (8H, m), 8.40 (1H, t, J=13.6 Hz); $^{13}$C NMR: (150.9 MHz, DMSO-$d_6$) δ=25.12, 27.32, 36.38, 41.96, 48.92, 102.33, 111.31, 122.52, 125.35, 128.51, 140.51, 141.62, 150.15, 174.23.

Example 2

In example 2, the permanent charge is part of the fluorophore that resides on the pyridinium moiety. The incipient cations are linked to the fluorophore via propylene groups.

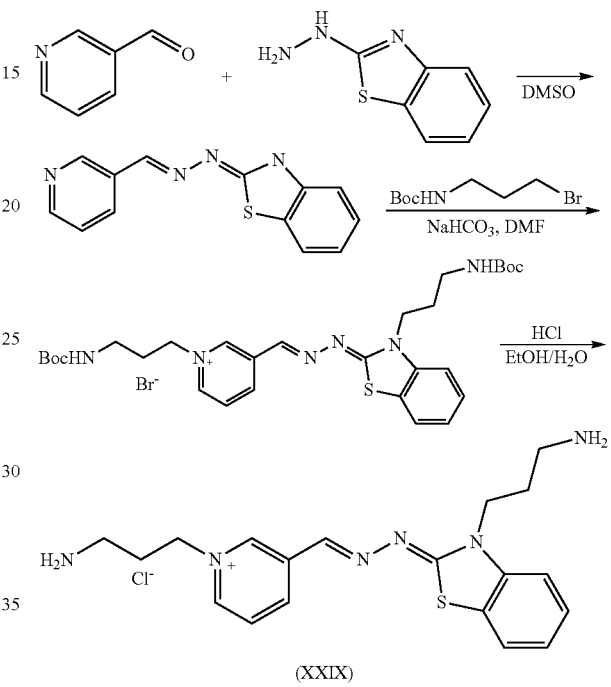

Nicotinaldehyde (1.07 g) was mixed with 2-hydrazinylbenzo[d]thiazole (1.0 eq., 1.65 g) in DMSO (15 mL) and stirred magnetically overnight. The resulting pale yellow slurry was dumped into ice-water and then filtered. The yellow cake collected from filtration is the desired intermediate. A portion of the intermediate, (Z)-2-(((E)-pyridin-3-ylmethylene)hydrazono)-2,3-dihydrobenzo[d]thiazole (0.5 g), was dissolved in DMF (15 mL) and reacted with 3-((t-butoxycarbonyl)amino)propyl bromide (2.1 eq.) and sodium bicarbonate (1.5 eq.). The reaction mixture was heated to 80° C. and magnetically stirred overnight. After the bisalkylation was complete, the Boc protection group was removed by adding concentrated aqueous HCl solution to the crude reaction mixture. DMF and water was then removed under vacuum. The resulting crude reaction mixture was purified on preparative reverse phase HPLC with water/methanol (with 0.1% TFA) as mobile phase. The final product (XXIX) was collected as its corresponding trifluoroacetate salt.

Exemplary Formulations

| | % by weight |
|---|---|
| Composition A | |
| Washfast Fluorescent Compound | 0.50 |
| Ammonium Hydroxide (aq. 28% active) | 4.50 |
| Water | 95.00 |

-continued

| | % by weight |
|---|---|
| Composition B | |
| Washfast Fluorescent Compound | 0.50 |
| Ammonium carbonate | 10.00 |
| Water | 89.50 |
| Composition C | |
| Washfast Fluorescent Compound | 0.50 |
| FlexiThix™ | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | 89.80 |
| Composition D | |
| Washfast Fluorescent Compound | 0.50 |
| Aculyn™ 46 | 15.80 |
| Phenoxyethanol | 0.30 |
| Sodium Benzoate | 0.30 |
| Disodium EDTA | 0.10 |
| Ammonium Hydroxide (aq. 28% active) | 4.00 |
| Water | 79.00 |
| Composition E | |
| Washfast Fluorescent Compound | 0.50 |
| Plantaren® 2000 N UP | 20.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | 74.80 |
| Composition F | |
| Washfast Fluorescent Compound | 0.50 |
| Non-anionic foaming agent | 5.00 |
| Phenoxyethanol | 0.30 |
| Sodium Benzoate | 0.30 |
| Disodium EDTA | 0.10 |
| Ammonium Hydroxide (aq. 28% active) | 4.00 |
| Water | 89.80 |

The compositions of the invention may be formed as thick liquid, cream, gel, emulsion, foam, aerosol mousse or as a solid form to which water is added to generate the oxidant and form a thickened vehicle suitable for hair treatment. They may comprise in addition to the ingredients indicated above further ingredients in order to further enhance the properties of the composition, including but not limited to: solvents; oxidative dyes, direct dyes; oxidizing agents; radical scavengers; thickeners and or rheology modifiers; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; enzymes; dispersing agents; peroxide stabilizing agents; antioxidants; natural ingredients, e.g. proteins and protein compounds, and plant extracts; conditioning agents including silicones and cationic polymers, ceramides, preserving agents; and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A few of these ingredients are discussed hereinbelow, whose disclosure is of course non-exhaustive.

Other Ingredients

The composition according to the present invention may comprise, in addition to the ingredients indicated above, further ingredients in order to further enhance the properties of the composition, as long as these are not excluded by the claims.

Suitable further ingredients include, but not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof. Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The composition according to the present invention may further comprise a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polyglycerol); propylene carbonate; and mixtures thereof.

In one embodiment, the solvent may be selected from the group consisting of water, ethanol, propanol, isopropanol, glycerol, 1,2-propylene glycol, hexylene glycol, ethoxy diglycol, and mixtures thereof.

Typically, the composition may comprise water as a main ingredient, particularly in a total amount ranging from at least about 50%, alternatively from at least about 60%, alternatively from at least about 70%, by weight of the total composition. Typically, when present, the composition comprises a total amount of organic solvents ranging from about 1% to about 30%, by weight of the total composition.

Oxidizing Agent

The composition may comprise at least one source of an oxidizing agent. Preferred oxidizing agents for use herein are water soluble peroxygen oxidizing agents. Water-soluble peroxygen oxidizing agents are well known in the art and include, but are not limited to, hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulfates and the like. These inorganic perhydrate salts may be incorporated as monohydrates, tetrahydrates etc. Alkyl and aryl peroxides, and or peroxidases, oxidases, and uricases and their substrates may also be used. Mixtures of two or more such oxidizing agents can also be used if desired. The oxidizing agents may be provided in aqueous solution or as a powder which is dissolved prior to use. Preferred for use in the compositions are hydrogen peroxide, percarbonate, persulfates and combinations thereof.

In one embodiment, the composition comprises from 0.1% to 20% by weight, or from 1% to 15% by weight, or from 2% to 10% by weight of oxidizing agent.

A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Preferred sources of carbonate ions, carbamate and hydrocarbonate ions are sodium hydrogen carbonate, potassium hydrogen carbonate, ammonium carbamate, and mixtures thereof.

The oxidative agent may comprise from 0.1% to 15% by weight, or from 1% to 10% by weight, or from 1% to 8% by weight of a hydrogen carbonate ion; and from 0.1% to 10% by weight, or from 1% to 7% by weight, or from 2% to 5% by weight of the oxidative agent of a source of hydrogen peroxide.

Alkalizing Agent

The composition may further comprise, generally in the fluorophore component, an alkalizing agent as known in the art. Any alkalizing agent known in the art may be used such as ammonia, alkanolamines for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. Typical alkalizing agents are ammonia and/or monoethanolamine.

Typically, the compositions for the oxidative treatment of keratin fibers comprise from about 0.1% to about 10%, preferably from about 0.5% to about 6%, more preferably from about 1% to about 4% by weight of the alkalizing agent relative to the total weight of the composition.

The compositions described above may have a pH of from 7 to 12, preferably from 8 to 11. For embodiments comprising a peroxymonocarbonate ion, the pH is preferably up to and including pH 9.5, more preferably from 7.5 to 9.5, even more preferably from 8.4 to 9.5, most preferably from 8.5 to 9.4, for example, 9.0 or 9.3.

Any sub-components of the compositions, such as a fluorophore composition or an oxidizing composition, may have a different pH from the fluorophore composition. For example, if the fluorophore composition comprises an alkalizing agent, the fluorophore composition will have an alkaline pH, such as higher than 7. The oxidizing composition may comprise an acidic pH of less than 7.

When the composition of the present invention is obtained by mixing a developer and a fluorophore composition prior to use, the alkalizing agent is generally present in the fluorophore composition.

Oxidative Dye Precursors

In addition to the fluorophores of the invention, the composition according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the composition may comprise a total amount of oxidative dye precursors ranging up to about 12%, alternatively from about 0.1% to about 10%, alternatively from about 0.3% to about 8%, alternatively from about 0.5% to about 6%, by weight of the total composition. Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(4-aminophenylamino)ethylazanediyl)diethanol, 2-(2,5-diamino-4-methoxyphenyl) propane-1,3-diol, 2-(7-amino-2H-benzol[b][1,4]oxazin-4 (3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, (2,3-diamino-6,7-dihydro-1H,5H-pyrazolo[1,2-a]pyrazol-1-one dimethanesulfonate), 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis (azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the composition of the invention is obtained by mixing a fluorophore composition and a developer composition, the primary intermediates and couplers are usually incorporated into the fluorophore composition.

Direct Dyes

The composition according to the present invention may further comprise compatible direct dyes, in an amount sufficient to provide additional coloring, particularly with regard to intensity. Typically, the composition may comprise a total amount of direct dyes ranging from about 0.05% to about 4%, by weight of the total composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyediazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyediethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the composition is obtained by mixing a fluorophore composition and a developer composition, the direct dyes are usually incorporated into the fluorophore composition.

Chelants

The composition according to the present invention may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and AE Martell & RD Hancock, Metal Complexes in Aqueous Solution, Plenum Press, New York & London (1996), both incorporated herein by reference.

Typically, the composition may comprise a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof. Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—PO3H2) or its derivative —PO3R2, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylenediamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

In a specific embodiment, the composition comprises a chelant selected from the group consisting of diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the composition of the invention is obtained by mixing a fluorophore composition and a developer composition, the chelants may be incorporated in the fluorophore composition and/or in the developer composition. A chelant is usually present in the developer composition for stability reason.

Radical Scavengers

According to the present invention, the compositions may comprise a radical scavenger. As used herein the term radical scavenger refers to a species that can react with a radical, to convert the radical species by a series of fast reactions to an unreactive or less reactive species. The radical scavenger is also preferably selected such that it is not an identical species as the alkalising agent and is present in an amount sufficient to reduce the damage to the hair during the colouring/bleaching process. The compositions of the present invention comprise a radical scavenger from about 0.1% to about 10%, preferably from about 1% to about 7% by weight of the radical scavenger relative to the total weight of the composition.

Suitable radical scavengers for use herein may be selected from the classes of alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)-pyrazol-5-one, 1,3-diphenyl-pyrazol-5-one, methyl pyrazol-5-one-3-carboxylate, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof. In some embodiments, the inventive compositions may comprise glycine, sarcosine, lysine, serine, 2-methoxyethylamine, glucosamine, glutamic acid, morpholine, piperidine, ethylamine, 3-amino-1-propanol, or mixtures thereof.

pH Modifiers and Buffering Agents

The composition according to the present invention may further comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The composition according to the invention may further comprise a thickener in an amount sufficient to provide the composition with a viscosity so that it can be readily applied to the hair without unduly dripping off the hair and causing mess.

Typically, the composition may comprise a total amount of thickeners ranging from at least about 0.1%, alternatively at least about 1%, alternatively at least about 10%, alternatively at least about 20%, by weight of the total composition.

Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof. Commercially available anionic materials include those sold as Sepigel 305 by Seppic.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (XXX) below CH2=C(R1)CH2OBnR            (XXX)

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (XXXI) below

CH2=C(R1)COOH            (XXXI)

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (XXXII) below CH2=C(R1)COOBnR2            (XXXII)

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (XXXIII) below

CH2=C<            (XXXIII)

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

Preferred associative polymers comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculyn-22 by Rohm & Haas; Permulen TR1, Carbopol 2020, Carbopol Ultrez-21/-30 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/1382/2984/5984 by Noveon, Synthalen M/Synthalen L/Synthalen K/Synthalen CR by 3V, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (hydroxypropyl guar) and bio-polysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., all three being incorporated herein by reference. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch, a hydrophobically modified cellulose derivative, commercially available as Structure® Cel 500 HM by AkzoNobel.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), polyvinylpyrrolidone (Povidone, FlexiThix™), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth—10 phosphate, Dicetyl phosphate and Cetearyl alcohol (available as Crodafos CES), and mixtures thereof.

Carbonate Ion Sources

The composition according to the present invention may further comprise a source of carbonate ions, carbamate ions, hydrogen carbonate ions, and mixtures thereof in a sufficient amount to reduce damage to the hair during the process.

Typically, the composition may comprise a total amount of a carbonate ion source ranging from about 0.1% to about 15%, alternatively from about 0.1% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The composition according to the present invention may further comprise a conditioning agent, and/or be used in combination with a composition comprising a conditioning agent.

Typically, the composition may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane $(Si(CH_3)_2$—O) units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be $(CH_3)_3Si$—O, $R_{12}(CH_3)_2Si$—O, where $R_{12}$ can be either OH or $OR_{13}$, where $R_{13}$ is a C1-C8 alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5 \times 10^6$, alternatively from about 1000 to about $3 \times 10^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinyllactams such as vinlypyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); coplymers of vinyl pyrrolidone and dialkyaminoalkyl acrylates or methactylates, including polymers known as Polquaternium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [-N+(R1)(R2)-A1–N+(R3)(R4)–B1-][2X-], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax).

7) Polyquaternary ammonium polymers comprising repeating units of formula [-lines N+(R6)(R7)-(CH2)r-NH—CO—(CH2)q-(CO)t-NH—(CH2)s-N+(R8)(R9)-A-] [2X-], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X– is anion such as a halide. T is an integer chosen to be equal to 0 or 1. A is chosen from divalent radicals such as —CH2-CH2-O—CH2-CH2-. Suitable examples include: polymers known as polyquaternium-2, where r=s=3, q=0, t=0, R6, R7, R8 and R9 are methyl groups, and A is —CH2-CH2-O—CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-CH2-O—CH2-CH2; as Polyquaternium 18, where r=s=3, q=7, t=1 R6, R7, R8 and R9 are methyl groups, and A is —CH2-CH2-O—CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12 (CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

In a preferred embodiment, the cationic polymer is selected from the group consisting of polyquaternium 37, polyquaternium 7, polyquaternium 22, polyquaternium 87, and mixtures thereof; particularly from the group consisting of polyquaternium 37, polyquaternium 22, and mixtures thereof.

Surfactants

The composition according to the present invention may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

Typically, the composition may comprise a total amount of surfactants ranging from about 0.01% to about 60%, alternatively from about 0.05% to about 30%, alternatively from about 0.1% to about 25%, alternatively from about 0.1% to about 20%, by weight of the total composition.

The compositions may comprise a mixture of an anionic surfactant and an amphoteric surfactant with one or more nonionic surfactants. The composition may comprise a total amount of anionic surfactant ranging from about 0.01% to about 20%, alternatively from about 0.05% to about 15%, alternatively from about 0.1% to about 15%, by weight of the total composition; and a total amount of amphoteric and/or nonionic components, which may range independently from each other from about 0.01% to about 15%, alternatively from about 0.05% to about 10%, alternatively from about 0.1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylaryl-polyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold as Miranol, as described, for example, in U.S. Pat. Nos. 2,528,378 and 2,781,354 and having the structures of: $R_2$—CON HCH$_2$CH$_2$—N$^+$(R$_3$)(R$_4$)(CH$_2$COO$^-$), (XXXIV) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—CONHCH$_2$CH$_2$—N(B)(C) (XXXV) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary ammonium salts of general formula (XXXVI) below:

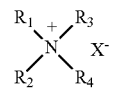

(XXXVI)

wherein X$^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from $(C_{12}$-$C_{22})$alkylamido$(C_2$-$C_6)$alkyl and $(C_{12}$-$C_{22})$ alkylacetate radicals. A suitable cationic surfactant is, for example, a dicetyldimethyl ammonium salt (for example chloride);

B) Quaternary ammonium salts of imidazolinium of formula (XXXVII) below:

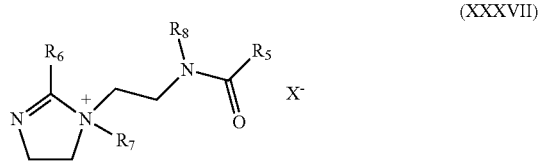

(XXXVII)

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and $X^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (XXXVIII):

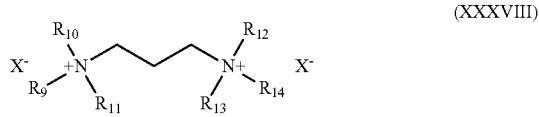

(XXXVIII)

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowdiammonium dichloride.

D) Quaternary ammonium salts comprising at least one ester function, of formula (XXXIX) below:

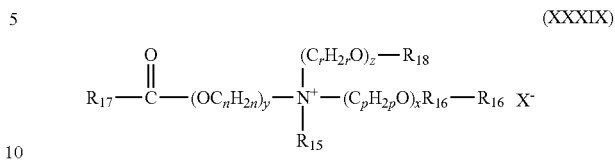

(XXXIX)

in which: R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X– is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XXXX) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of imparting improved washfastness when treating the hair fluorescent compounds, the method comprising:
   a. applying to the hair a fluorescent material composition comprising one or more fluorescent compounds, the one or more fluorescent compounds each comprising a fluorescent compound of Formula V, Formula VIII, Formula X, Formula XII, Formula XIV, Formula XVI, Formula XXVI, Formula XXVII, homologs thereof, the partially or fully protonated forms thereof, or any combination thereof wherein these Formulas and homologs thereof have the following structures:

Formula V

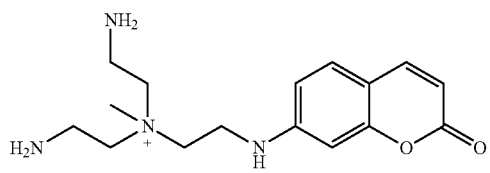

or a homolog thereof wherein one, two or three of the ethylenyl linkers bonded to the quaternary nitrogen are replaced by a propylenyl linker group;

Formula VIII

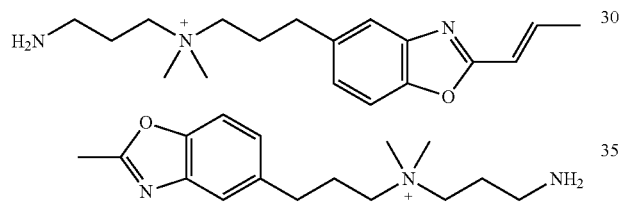

or a homolog thereof wherein one, two, three, or four of the propylenyl linkers bonded to either or both of the quaternary nitrogens are replaced by an ethylenyl linker group;

Formula XI

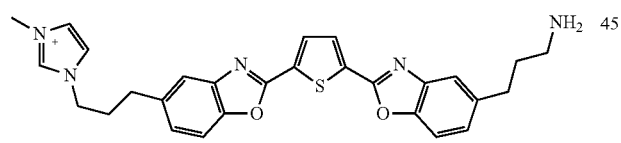

or a homolog thereof wherein one or both of the propylenyl linkers bonded to the benzoxazolyl groups are replaced by an ethylenyl linker group;

Formula XIII

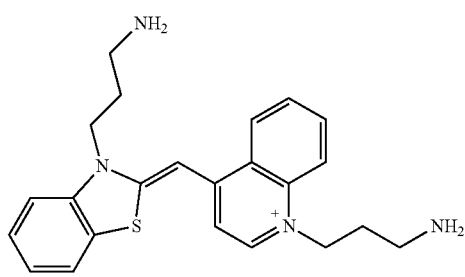

or a homolog thereof wherein the one or both of the propylenyl linkers bonded to the quinolinyl group or the propylenyl linker bonded to the benzothiazolyl group are replaced by an ethylenyl linker group;

Formula XVI

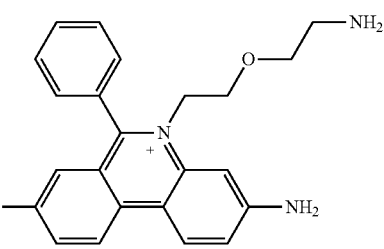

or a homolog thereof wherein one or both of the propylenyl linkers bonded to the oxygen are replaced by an ethylenyl linker group;

Formula XVIII

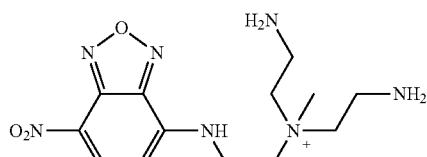

or a homolog thereof wherein one, two, or three of the ethylenyl linkers bonded to the quaternary nitrogen are replaced by a propylenyl linker group;

Formula XXVIII

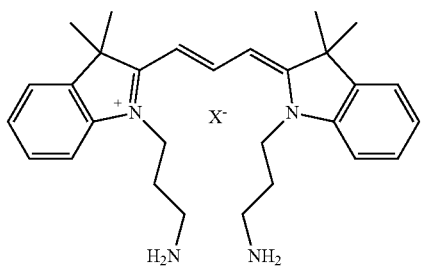

or a homolog thereof wherein one or both of the propylenyl linkers bonded to the nitrogen of the indolyl groups are replaced by an ethylenyl linker group;

Formula XXIX

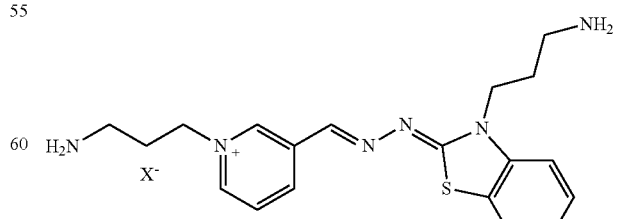

or a homolog thereof wherein one or both of the propylenyl linker bonded to the nitrogen of the benzothiazolyl group and the propylenyl linker bonded to the nitrogen of the pyridinyl group is replaced by an ethylenyl linker group; and,
   wherein the composition has a pH of from about 7 to about 11;
   wherein the one or more fluorescent compounds enter the hair shaft after the composition is applied to the hair; and
b. rinsing the hair with water;
   wherein the pH of the hair after rinsing is from about 3.5 to about 6.

2. The method of claim 1, wherein the one or more fluorescent compounds each comprise two incipient cations.

3. The method of claim 1, wherein the one or more fluorescent compounds each has a molecular weight of less than about 1,000 g/mol.

4. The method of claim 1, wherein the hair treatment composition further comprises one or more oxidative dye precursors.

5. The method of claim 1, wherein the hair treatment composition further comprises one or more direct dyes.

6. The method of claim 1, wherein the hair treatment composition has a pH of from about 9 to about 11.

7. The method of claim 1, wherein the hair treatment composition has a pH of from about 7 to about 9.

8. The method of claim 1, wherein the one or more fluorescent compounds is an optical brightening compound.

9. The method of claim 1, wherein an oxidizing agent is applied before or during the application of the hair treatment composition.

10. The method of claim 9, wherein the oxidizing agent is selected from the group consisting of peroxides, perborates, percarbonates, persulfates, peroxidases and their substrates, laccases and their substrates, uricases and their substrates, oxidases and their substrates, and combinations thereof.

* * * * *